United States Patent [19]
Corley, Jr.

[11] Patent Number: 6,153,230
[45] Date of Patent: Nov. 28, 2000

[54] COVER SCENT AND WILD GAME LURE

[76] Inventor: Samuel O. Corley, Jr., 894 Liberty Rd., Natchez, Miss. 39120

[21] Appl. No.: 09/383,976

[22] Filed: Aug. 26, 1999

Related U.S. Application Data

[60] Provisional application No. 60/098,641, Aug. 31, 1998.
[51] Int. Cl.⁷ ....................................................... A23L 1/221
[52] U.S. Cl. ................................ 426/1; 426/425; 426/489
[58] Field of Search ................................ 426/1, 425, 655, 426/489; 424/84

[56] References Cited

U.S. PATENT DOCUMENTS 5,415,862  5/1995  Bethshears et al. .................. 424/84 X

*Primary Examiner*—Milton Cano
*Attorney, Agent, or Firm*—Sieberth & Patty, L.L.C.

[57] ABSTRACT

A composition which may serve as either a scent cover or a wild game lure. The composition is formed from ingredients comprising (a) an extract formed from a mixture of at least a portion of a Sassafras tree and at least a portion of a Honey Locust tree; (b) vanilla extract; and (c) ascorbic acid. Related processes and methods of use.

17 Claims, No Drawings

COVER SCENT AND WILD GAME LURE

REFERENCE TO RELATED APPLICATION

This application claims the benefit of U.S. Provisional Patent Application Ser. No. 60/098,641, file on Aug. 31, 1998.

TECHNICAL FIELD

The present invention relates to compositions of matter useful in providing cover scent and/or luring wild game, and related methods of use.

BACKGROUND

Several attempts have been made to develop cover scents which mask the presence of the wearer to those with a keen sense of smell, e.g., deer, elk or other wild game. Additionally, many have attempted to develop a composition of matter which attracts wild game so as to bring the game toward the vicinity of the composition. However, many of the compositions of matter previously developed as cover scents and/or wild game lures either are fabricated from synthetic materials which do not easily degrade in the natural environment, or are simply ineffective to actually cover scent or lure wild game.

Thus, a need continues to exist for a composition which can effectively lure wild game and/or provide a cover scent to a user, all while being formed from completely biodegradable materials.

SUMMARY OF THE INVENTION

The present invention is deemed to satisfy this need in a particularly elegant and effective way. In one aspect of this invention, a composition of matter is provided which is formed from ingredients comprising (a) an extract formed from a mixture of at least a portion of a Sassafras tree (e.g., Sassafras Albidum or equivalents) and at least a portion of a Honey Locust tree (e.g., Gleditsia Triacanthos or equivalents); (b) vanilla extract; and (c) ascorbic acid.

In another aspect of this invention, a process for preparing a composition for use as a cover scent and/or wild game lure is provided. The process comprises (a) heating a mixture comprised of water, a portion of a Sassafras tree and a portion of a Honey Locust tree to form an extract; (b) forming an aqueous solution of the extract; and (c) mixing together vanilla extract, ascorbic acid and the aqueous solution.

These and other embodiments of this invention will be further appreciated from the ensuing description of preferred embodiments and the appended claims.

DETAILED DESCRIPTION OF PREFERRED EMBODIMENTS

The compositions of this invention are formed from ingredients which are comprised of naturally produced materials so as to provide an environmentally friendly product and to increase wild game affinity for the product by removing product dependence upon synthetic or exotic ingredients which may be noticeably unfamiliar to wild game.

In particular, it is especially preferred that water used in the compositions of this invention be untreated spring water or rain water, to decrease the likelihood that compounds foreign to wild game are present in the composition. Likewise, it is especially preferred that substantially pure and natural vanilla extract be used in compositions of this invention.

In processes of this invention for preparing a composition for use as a cover scent and/or wild game lure, it should be noted that the particular relative proportions of the ingredients may vary, depending upon the ingredients selected and the source of those natural ingredients. While it may be desirable to test the relative proportions to optimize the same, such tests will be well within the capabilities of those with ordinary skill in the art. In particularly preferred embodiments, the amount of vanilla extract is two tablespoons per gallon of aqueous solution. Likewise, the amount of ascorbic acid is most preferably 250 mg per gallon of aqueous solution. In addition, in particularly preferred embodiments, the portion of the Sassafras tree employed in this invention is the root. Likewise, the portion of the Honey Locust tree is most preferably the complete seed pod.

It should also be appreciated that the amount of heating and duration of heating applied to boil or pressure cook mixtures in the processes of this invention may vary depending upon the relative proportions of ingredients and the surrounding ambient physical conditions, and so long as the amount of heat and time selected results in an extract with a detectable scent, optimizing heat and duration of heating should be well within the capability of the person of ordinary skill in the art.

The following illustrates the production of a preferred composition of this invention.

EXAMPLE

A section of a dried mature root from a Sassafras Tree (e.g., Sassafras Albidum) and several dried complete mature seed pods from a Honey Locust Tree (e.g., Gleditsia Triacanthos) were boiled in clean pure water to extract the essence of each of the above. The resulting essence was added to enough clean, pure water to make one (1) gallon of liquid. To this gallon of liquid was added two (2) tablespoons of pure vanilla extract and 250 mg of ascorbic acid, the liquid mixture thus obtained being mixed thoroughly. The mixture was bottled, capped, sealed and stored to keep it from freezing, direct heat and sunlight.

As will now be appreciated, wild game may be lured to a given location when compositions of this invention are applied to the location (i.e., applied directly to the location or to a different location in sufficient proximity to the desired location so as to obtain the desired effect). In addition, the scent of an object (e.g., a human) may be covered by applying a composition of this invention to the object (i.e., applying directly to the object or to a location in sufficient proximity to the object so as to obtain the desired effect). Such objects can include, for example, the ground, clothes, equipment, drag rags, trees, plants, canisters, dispensing apparatus, or the like. Compositions of this invention may also be used to attract wild game to trap sets and to cover other scents at the trap set.

This invention is susceptible to considerable variation in its practice. Therefore, the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A composition which is formed from ingredients comprising:

a) an extract formed from a mixture of at least a portion of a Sassafras tree and at least a portion of a Honey Locust tree;

b) vanilla extract; and c) ascorbic acid.

2. The composition of claim 1 wherein the portion of the Sassafras tree is at least one segment of the Sassafras tree root.

3. The composition of claim 2 wherein the portion of the Honey Locust tree is one or more seed pods from the Honey Locust tree.

4. The composition of claim 3 wherein the ingredients further comprise water.

5. The composition of claim 1 wherein the portion of the Honey Locust tree is one or more seed pods from the Honey Locust tree.

6. A method of luring wild game to a given location, which method comprises applying a composition of claim 1 to the location.

7. A method of luring wild game to a given location, which method comprises applying a composition of claim 4 to the location.

8. A method of covering the scent of an object, which method comprises applying a composition according to claim 1 to the object.

9. A method of covering the scent of an object, which method comprises applying a composition of claim 4 to the object.

10. A process for preparing a composition for use as a cover scent and/or wild game lure, the process comprising:

a) heating a mixture comprised of water, a portion of a Sassafras tree and a portion of a Honey Locust tree to form an extract;

b) forming an aqueous solution of the extract; and c) mixing together vanilla extract, ascorbic acid and the aqueous solution.

11. A process according to claim 10, wherein the portion of the Sassafras tree is at least one segment of the Sassafras tree root.

12. A process according to claim 10, wherein the portion of the Honey Locust tree is a plurality of seed pods from the Honey Locust tree.

13. A process according to claim 10, wherein the amount of vanilla extract is two tablespoons per gallon of the aqueous solution.

14. A process according to claim 13, wherein the amount of ascorbic acid is 250 mg per gallon of the aqueous solution.

15. A process according to claim 14, wherein the portion of the Sassafras tree is at least one segment of the Sassafras tree root.

16. A process according to claim 15, wherein the portion of the Honey Locust tree is a plurality of seed pods from the Honey Locust tree.

17. A process according to claim 10, wherein the amount of ascorbic acid is 250 mg per gallon of the aqueous solution.

\* \* \* \* \*